United States Patent [19]

Yoon

[11] Patent Number: 5,665,072

[45] Date of Patent: Sep. 9, 1997

[54] SAFETY NEEDLE INSTRUMENT WITH MOVABLE CANNULA AND NEEDLE

[76] Inventor: InBae Yoon, 2101 Highland Ridge Dr., Phoenix, Md. 21131

[21] Appl. No.: 371,558

[22] Filed: Jan. 11, 1995

Related U.S. Application Data

[63] Continuation-in-part of Ser. No. 247,205, May 20, 1994, and a continuation-in-part of Ser. No. 254,007, Jun. 3, 1994, Pat. No. 5,478,317, said Ser. No. 247,205, May 20, 1994, is a division of Ser. No. 800,507, Nov. 27, 1991, abandoned, said Ser. No. 254,007, Jun. 3, 1994, Pat. No. 5,478,317, is a continuation of Ser. No. 800,507, Nov. 27, 1991, abandoned, Ser. No. 79,586, Jun. 22, 1993, and Ser. No. 260,439, Jun. 15, 1994, Pat. No. 5,423,760, which is a division of Ser. No. 868,578, Apr. 15, 1992, Pat. No. 5,336,176, and Ser. No. 237,734, May 4, 1994, abandoned, which is a continuation of Ser. No. 868,578, Apr. 15, 1992.

[51] Int. Cl.$^6$ .................................................. A61M 5/00
[52] U.S. Cl. ................................................................ 604/164
[58] Field of Search ...................................... 604/164, 165

[56] References Cited

U.S. PATENT DOCUMENTS

| Re. 32,922 | 5/1989 | Levin et al. |
|---|---|---|
| 1,527,291 | 2/1925 | Zorraquin. |
| 2,496,111 | 1/1950 | Turkel. |
| 2,623,521 | 12/1952 | Shaw. |
| 2,630,803 | 3/1953 | Baran. |
| 4,254,762 | 3/1981 | Yoon. |
| 4,345,589 | 8/1982 | Hiltebrandt. |
| 4,442,836 | 4/1984 | Meinecke et al. |
| 4,488,545 | 12/1984 | Shen. |
| 4,503,856 | 3/1985 | Cornell et al. |
| 4,535,773 | 8/1985 | Yoon. |
| 4,559,041 | 12/1985 | Razi. |
| 4,601,710 | 7/1986 | Moll. |
| 4,627,841 | 12/1986 | Dorr. |
| 4,654,030 | 3/1987 | Moll et al. |
| 4,670,008 | 6/1987 | Von Albertini. |
| 4,677,979 | 7/1987 | Burns. |
| 4,747,831 | 5/1988 | Kulli. |
| 4,802,275 | 2/1989 | Haber et al. |
| 4,817,603 | 4/1989 | Turner et al. |
| 4,869,717 | 9/1989 | Adair. |
| 4,889,117 | 12/1989 | Stevens. |
| 4,900,307 | 2/1990 | Kulli. |
| 4,902,280 | 2/1990 | Lander. |
| 4,906,236 | 3/1990 | Alberts et al. |
| 4,931,042 | 6/1990 | Holmes et al. |
| 4,943,280 | 7/1990 | Lander. |

(List continued on next page.)

FOREIGN PATENT DOCUMENTS

| 2544262 | 4/1977 | Germany. |
|---|---|---|
| 1435246 | 11/1988 | U.S.S.R. |

Primary Examiner—Todd E. Manahan

[57] ABSTRACT

A safety needle instrument for establishing a portal in the wall of an anatomical cavity includes a housing, an elongate cannula movable relative to the housing between an extended rest position and a retracted position and having a proximal end mounted by the housing and a distal end for introduction in the anatomical cavity, a cannula bias member for biasing the cannula distally toward the cannula extended position, a needle disposed within the cannula and movable relative thereto between an extended position and a retracted position where the needle distal end is proximally spaced from the cannula distal end, a retracting mechanism for moving the needle from the needle extended position to the needle retracted position, a handle for manually moving the needle from the needle retracted position to the needle extended position, a locking mechanism for locking the needle in the needle extended position while permitting a predetermined amount of proximal movement of the needle during penetration of the anatomical cavity wall, a needle bias member for biasing the needle distally in the needle extended position while permitting the needle to move proximally during penetration of the anatomical cavity wall, and a releasing mechanism responsive to penetration of the safety needle instrument into the anatomical cavity for triggering release of the locking means to permit the retracting means to move the needle proximally to the needle retracted position.

12 Claims, 7 Drawing Sheets

U.S. PATENT DOCUMENTS

| | | |
|---|---|---|
| 4,946,446 | 8/1990 | Vadher . |
| 4,955,870 | 9/1990 | Ridderheim et al. . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deniega et al. . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,127,909 | 7/1992 | Shichman . |
| 5,129,885 | 7/1992 | Green et al. . |
| 5,152,754 | 10/1992 | Plyley et al. . |
| 5,158,552 | 10/1992 | Borgia et al. . |
| 5,207,647 | 5/1993 | Phelps . |
| 5,226,426 | 7/1993 | Yoon . |
| 5,226,891 | 7/1993 | Bushatz et al. . |
| 5,290,243 | 3/1994 | Chodorow et al. . |
| 5,290,304 | 3/1994 | Storace . |
| 5,295,993 | 3/1994 | Green . |
| 5,312,354 | 5/1994 | Allen et al. . |
| 5,318,580 | 6/1994 | Gresl, Jr. . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,342,382 | 8/1994 | Brinkerhoff et al. . |
| 5,346,459 | 9/1994 | Allen . |
| 5,350,393 | 9/1994 | Yoon . |
| 5,360,405 | 11/1994 | Yoon . |
| 5,372,588 | 12/1994 | Farley et al. . |
| 5,376,082 | 12/1994 | Phelps . |

SAFETY NEEDLE INSTRUMENT WITH MOVABLE CANNULA AND NEEDLE

CROSS-REFERENCE TO RELATED APPLICATIONS

This application is a continuation-in-part of applications Ser. No. 08/247,205, filed May 20, 1994, and Ser. No. 08/254,007, filed Aug. 10, 1994, now U.S. Pat. No. 5,478,317 which are a divisional application and a continuation application, respectively, of application Ser. No. 07/800,507, filed Nov. 27, 1991 and now abandoned; Ser. No. 08/079,586, filed Jun. 22, 1993, now U.S. Pat. No. 5,423,770 and Ser. No. 08/260,439, filed Jun. 15, 1994, now U.S. Pat. No. 5,423,760 which are divisional applications of application Ser. No. 07/868,578, filed Apr. 15, 1992 now U.S. Pat. No. 5,336,176 and Ser. No. 08/237,734, filed May 4, 1994, now abandoned which is a continuation of application Ser. No. 07/868,578. The disclosures of the above patent applications are incorporated herein by reference.

BACKGROUND OF THE INVENTION

1. Field of the Invention

The present invention pertains to safety needle instruments and, more particularly, to safety needle instruments including needles having sharp tips for penetrating anatomical tissue to establish communication with anatomical cavities wherein tissue and organ structures are protected from the tips of the needles.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Such penetrating instruments typically include an outer sleeve or cannula and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring-biased to protrude beyond the tip of the penetrating member in response to the reduced force on the distal end of the safety member upon entry into the anatomical cavity. Safety needle instruments including a safety member in the form of a probe biased to protrude beyond the sharp tip of a needle have become widely accepted for use in penetrating anatomical cavities. For example, the Verres needle, commonly used to create a pneumoperitoneum, has a spring-loaded inner member disposed within a tubular needle. Safety trocars having a safety member in the form of a spring-biased protective shield disposed between an outer sleeve and an inner trocar are also known.

Retractable safety penetrating instruments typically include a trocar disposed within a portal sleeve and retractable within the sleeve in response to distally-biased movement of a component of the safety penetrating instrument, such as the trocar or the sleeve, caused by a reduction in force from tissue contact upon entering the anatomical cavity.

One of the limitations of many prior art safety needle instruments is that the safety probes can produce an irregular surface or profile with the sharp tips of the needles during penetration of tissue resulting in increased resistance during penetration of an anatomical cavity wall, trauma and damage to tissue and possible jamming of trapping of tissue. Another limitation of many prior art safety needle instruments is that very small or narrow anatomical cavities cannot be penetrated without protrusion of the safety probes from the sharp tips of the needles. A further limitation of many prior art safety needle instruments is that the needles cannot be automatically retracted to safe, protected positions wherein the sharp tips of the needles are disposed within the instruments upon penetration into anatomical cavities.

SUMMARY OF THE INVENTION

Accordingly, it is a primary object of the present invention to overcome the above-mentioned disadvantages of the prior art and to improve safety needle instruments of the type having a cannula and a needle.

An additional object of the present invention is to ease penetration by permitting both the needle and cannula of a safety needle instrument to move proximally in response to tissue contact during penetration of an anatomical cavity wall.

It is another object of the present invention to maintain distal ends of the needle and cannula of a safety needle instrument in substantially aligned positions to create a smooth distal surface or profile as the needle and cannula are moved proximally in response to tissue contact during penetration of an anatomical cavity wall.

A further object of the present invention is to minimize the likelihood of the needle of a safety needle instrument being retracted before the cannula has entered an anatomical cavity by conditioning retraction of the needle on distally-biased movement of the needle and the cannula in response to a reduction in force from tissue contact upon entering the anatomical cavity.

Some of the advantages of the present invention over the prior art are that penetration of an anatomical cavity wall can be achieved using a smooth and continuous movement, that penetration of an anatomical cavity wall can be commenced with the cannula in an extended rest position either shielding or exposing the tip of the needle as desired, that the risk of developing a hematoma when penetrating veins and arteries is reduced, that the safety needle instrument can be used in many various ways including, for example, as an infusion or aspiration syringe, an intravenous needle system, an insufflation needle, a catheter system, a biopsy system, an injection or irrigation system, an aspiration or drainage system, catheterization for blood, urine, bile, ovarian fluid, spinal fluid, pleural fluid and bowel or peritoneal fluid sampling, and that retraction of the needle of the safety needle instrument can be achieved in response to distally-biased movement of one or more movable members such that the safety and efficacy of the safety needle instrument is enhanced.

The present invention is generally characterized in a safety needle instrument for establishing a portal in the wall of an anatomical cavity including a housing, an elongate cannula movable relative to the housing between an extended rest position and a retracted position and having a proximal end mounted by the housing and a distal end for introduction in the anatomical cavity, cannula bias means for biasing the cannula distally toward the cannula extended position, a needle disposed within the cannula and movable relative thereto between an extended position where a distal end of the needle protrudes from the cannula distal end and a retracted position where the needle distal end is proximally spaced from the cannula distal end, retracting means for moving the needle from the needle extended position to the needle retracted position, means for manually moving the needle from the needle retracted position to the needle extended position, locking means for locking the needle in the needle extended position while permitting a predetermined amount of proximal movement of the needle during penetration of the anatomical cavity wall, needle bias means for biasing the needle distally in the needle extended position while permitting the needle to move proximally during penetration of the anatomical cavity wall, and releasing means responsive to penetration of the safety needle instrument into the anatomical cavity for triggering release of the locking means to permit the retracting means to move the needle to the needle retracted position. The releasing means of the safety needle instrument can be responsive to distally-biased movement of the needle, the cannula or both the needle and the cannula for triggering release of the locking means to permit retraction of the needle.

Other objects and advantages of the present invention will become apparent from the following description of the preferred embodiments taken in conjunction with the accompanying drawings wherein, unless specified otherwise, like parts or parts that perform like functions are identified in each of the several figures by the same reference numeral or by reference numerals sharing the same last two digits.

DESCRIPTION OF THE PREFERRED EMBODIMENTS

Figure 1:
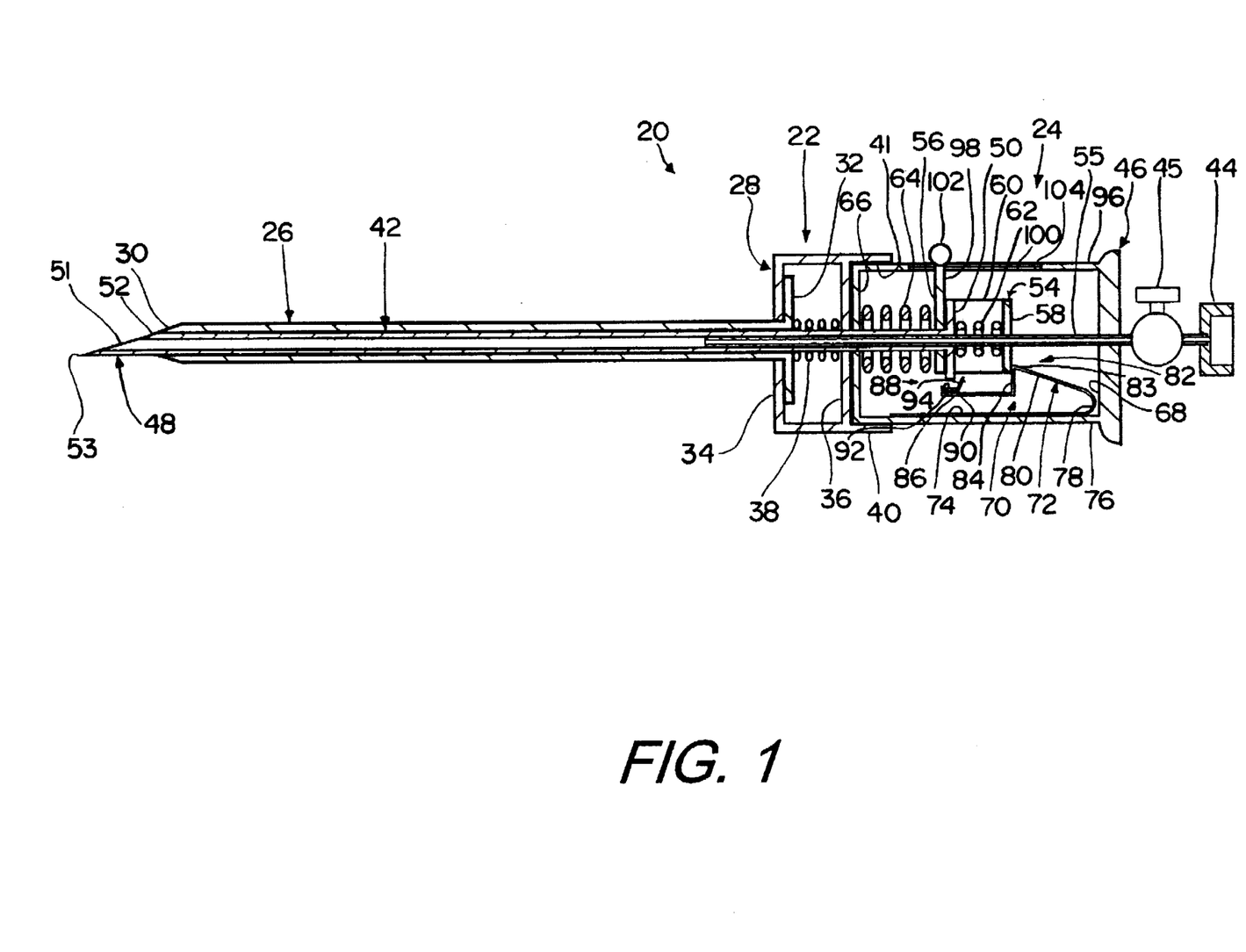
FIG. 1 is a side view, partly in section, of a safety needle instrument according to the present invention.

A safety needle instrument 20 according to the present invention, as shown in FIG. 1, is formed of a catheter or cannula unit 22 and a needle unit 24. The catheter unit 22 can be made of any desirable, medical grade materials depending on procedural use and desirability of being for single patient use or reusable. The catheter unit includes an elongate cannula 26 and a housing 28 mounting a proximal end of the cannula 26. Cannula 26 terminates distally at a distal end 30 and proximally at a flange 32 disposed between front and rear walls 34 and 36 of the housing 28. A bias member 38, in the form of a helical coil spring disposed around the longitudinal axis of the safety needle instrument and mounted in compression between the cannula flange 32 and the housing rear wall 36, biases the cannula 26 distally to cause flange 32 to abut the front wall of the housing. It will be appreciated, however, that other types of bias members can be used, including tension springs, compression springs, torsion springs, pan springs, rubber, plastic or magnets, for example.

Cannula 26 can have any desirable cross-sectional configuration, including cylindrical or tubular configurations, in accordance with the procedure to be performed and the anatomical cavity to be penetrated. Preferably, cannula 26 is made of a substantially cylindrical length of rigid or flexible and transparent or opaque material, such as a medically acceptable plastic or metal material, and has a tubular configuration defining a lumen between the distal and proximal cannula ends for receiving a needle 42 of needle unit 24. The cannula distal end 30 can have various configurations to protect tissue within an anatomical cavity by covering the distal tip of the needle with the cannula in the cannula extended position; and, as shown, the cannula distal end defines an annular or peripheral edge having a relatively blunt or chamfered configuration to ease penetration while protecting tissue within the anatomical cavity. The cannula can be provided with a shape or surface texture to increase resistance of the cannula to passage through anatomical tissue such that the cannula moves proximally against the bias of spring 38 during penetration of anatomical tissue by the safety needle instrument. The resistance of the cannula can be increased in many various ways such as by roughening, texturing or dimpling the external surface of the cannula or by providing the external surface with bumps, threads, ridges or other irregularities or by configuring the cannula to have a slight enlargement or protrusion.

Housing 28 can be made of any desirable material and can have any desirable configuration to facilitate grasping by a surgeon. As shown, front and rear walls 34 and 36 of the housing 28 are round and are joined by a generally cylindrical sidewall 40 that extends proximally beyond the housing rear wall in order to form a recess 41 for receiving the needle unit 24. Recess 41 can be configured to sealingly engage the distal end of the needle unit and other medical instruments, such as tubes, by friction fit, threaded engagement, Luer locks, detents or any other conventional coupling mechanism. An opening is formed in the housing rear wall 36 in axial alignment with an opening in the housing front wall 34 to allow passage therethrough by the needle 42 of needle unit 24; and, it will be appreciated that various valve mechanisms, such as trumpet or nipple valves, can be disposed within the housing 28 for sealingly engaging instruments, such as the needle 42, that pass through the housing.

Needle unit 24 includes an elongate hollow needle 42 open at proximal and distal ends and a hub 46 mounting the proximal end of the needle. The needle 42 terminates distally at a sharp distal end 48 and proximally at a transverse flange 50 disposed between walls of a rail member 54 mounted in the hub 46. The proximal end of the needle 42 is telescopically fitted over a hollow cylindrical guide tube 55 extending through the rear wall 68 of the hub to terminate proximally at a cylindrical coupling 44. Like recess 41, coupling 44 can be configured to sealingly engage the distal ends of medical instruments by friction fit, threaded engagement, Luer locks, detents or any other conventional coupling mechanism. A valve 45, shown as a stopcock, is disposed intermediate the coupling 44 and the hub and can be used to regulate passage of fluids and objects through the guide tube and the needle. The needle distal end 48 includes an angled peripheral surface or bevel 51 which extends distally from a transverse dimensional transition or junction 52 to form a sharp tissue penetrating tip 53. Rail member 54 is movable within hub 46 and is generally U-shaped including a forward wall 56 disposed transverse or perpendicular to a longitudinal axis of the needle instrument, a rearward wall 58 in configuration parallel to forward wall 56 and a side wall 60 transversely joining the forward and rearward rail member walls. Flange 50 is disposed between the rail member forward and rearward walls with the rail member forward wall 56 having an opening therein allowing passage therethrough by the needle 42. The rail member forward and rearward walls are disposed parallel or substantially parallel to flange 50, and a bias member 62 is connected between needle flange 50 and the rail member rearward wall 58 to bias the needle distally. As shown, bias member 62 includes a helical coil spring disposed around the guide tube 55 and mounted in compression between flange 50 and the rail member rearward wall 58 to bias the needle 42 distally to cause flange 50 to abut the rail member forward wall 56. However, bias member 62 can include various other types of springs as well as other types of bias devices including compression springs, tension springs, torsion springs, pan springs, leaf springs, rubber, plastic or magnets, for example. A retracting member 64 is mounted between rail member forward wall 56 and a front wall 66 of hub 46 to bias the needle 42 in a proximal direction to a retracted position where distal end 48 of the needle is disposed proximally of the cannula distal end 30 as will be explained further below. The retracting member includes a helical coil spring disposed around the needle 42 and mounted in compression between the rail member forward wall 56 and the front wall 66 of the hub to bias the rail member 54 and, therefore, the needle 42, in a proximal direction to a retracted position where the distal end 48 of the needle is disposed proximally of the cannula distal end.

A locking and releasing mechanism 70 for locking the needle in an extended position, shown in FIG. 1, exposing the distal end 48 of the needle and for releasing the rail member 54 to allow the needle 42 to move to the retracted position includes a latch or locking spring 72, made of a strip of resilient material, formed to have a substantially flat base 74 secured to a bottom wall 76 of hub 46 and a bend 78 joining the proximal end of the base 74 with an upwardly angled arm 80 spaced from the base. Arm 80 carries or forms a latch 82 having a proximal angled latching surface 83 joining a distal latching surface 84 disposed substantially transverse to the longitudinal axis of the safety needle instrument and substantially parallel to the rail member forward wall 56. Arm 80 has an extension 86 positioned distally of latch 82, and a releasing member or trigger 88 is juxtaposed with extension 86. The trigger 88 is pivotally mounted in the hub on a pin 90 secured to a wall or walls of the hub or structure supported in the hub, and the trigger is generally L-shaped with a leg 92 overlying extension 86 and a leg 94 extending transversely from leg 92 but at a slight angle toward the proximal end of the safety needle instrument. A torsion spring (not shown) is coiled around pin 90 and fixed to trigger 88 to bias the trigger counterclockwise, looking at FIG. 1, such that leg 92 is biased toward extension 86.

Rail member forward wall 56 extends toward a top wall 96 of the hub and a post 98 extends from the rail member forward wall through a longitudinal slot 100 formed in the top wall of the hub to terminate at a handle or knob 102 disposed within an elongate trough-like recess 104. Handle 102 can be grasped and manually moved distally along the slot formed in the top wall of the hub to move the needle from the retracted position to the locked extended position as previously explained above.

The catheter unit 22 and the needle unit 24 can be provided separately or assembled together as shown in FIG. 1, and either or both of the portal and needle units can be manufactured in a manner to be disposable for single patient use or to be sterilizable for re-use. The hub 46 can be coupled to the housing 28 by suitable detent or latch mechanisms if desired, and the needle unit can be withdrawn from the catheter unit leaving the cannula 26 in place within an anatomical cavity. Alternatively, the needle and catheter units can be formed as an integral one piece unit such that the needle remains in place within the cannula after being retracted.

Figure 3:
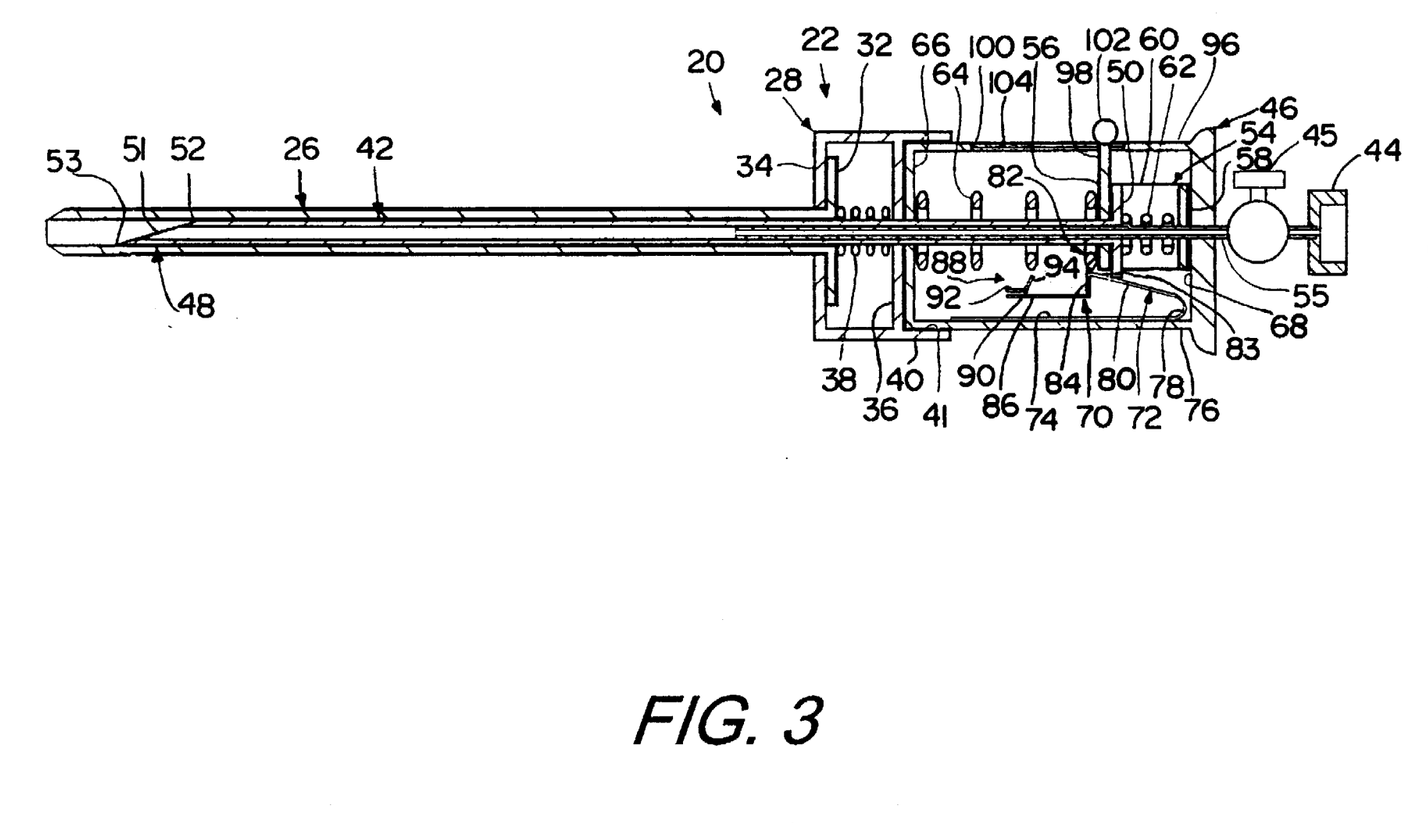
FIG. 3 is a side view, partly in section, of the safety needle instrument of FIG. 1 following penetration into an anatomical cavity wall.

In use, the safety needle instrument 20 can be provided in the condition illustrated in FIG. 3 with the cannula 26 in the extended rest position and the needle 42 in the retracted position where the distal end 48 of the needle is proximally spaced from the distal end 30 of the cannula to protect the sharp tip 53 of the needle. In order to move the needle to the extended position shown in FIG. 1, the handle 102 is grasped to move the rail member 54, and thus the needle 42, distally until the rail member rearward wall 58 rides over latch 82 to be latched in the extended position with the rail member rearward wall 58 locked against distal latching surface 84. The user can feel the rail member rearward wall 58 lock into place in engagement with the latch 82 and can also visually determine that the needle is in the locked extended position by noting the position of the handle 102 at a distal end of the slot 100.

Figure 2:
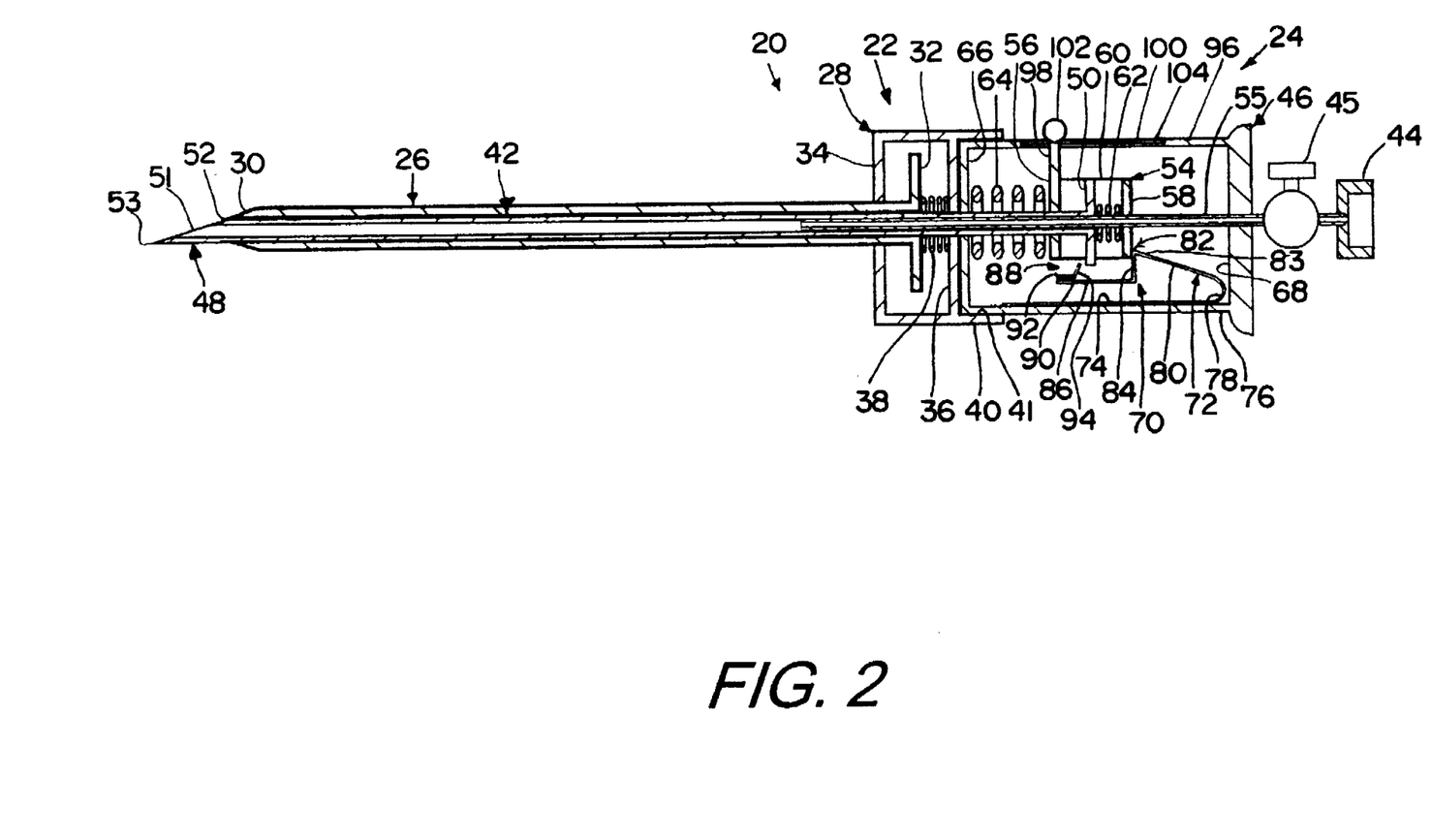
FIG. 2 is a side view, partly in section, of the safety needle instrument of FIG. 1 during penetration of an anatomical cavity wall.

With the needle 42 locked in the extended position illustrated in FIG. 1, the cannula distal end 30 can be disposed proximally of the distal tip 53 of the needle in alignment with the transverse dimensional transition or junction 52 to present a smooth profile for penetrating tissue such as the wall of a vein or artery. Needle 42 can move proximally against the bias of bias member 62 in the extended position in response to forces acting on the needle distal end, such as the force from tissue contact during penetration of an anatomical cavity wall. Proximal movement of the needle is limited by engagement of the needle flange 50 with the rearward wall 58 of the rail member, which serves as a stop or abutment. Similarly, cannula 26 can move proximally against the bias of bias member 38 in response to forces acting on the cannula distal end 30 until the cannula flange 32 abuts the housing rear wall 36. Since both the cannula and the needle are free to move proximally in response to tissue resistance during penetration, the alignment of the cannula distal end with the needle junction can be substantially maintained in order to ease penetration. When penetration of an anatomical cavity wall is commenced, therefore, the force from tissue contact on the cannula and needle distal ends 30 and 48 will cause the cannula and needle to move together proximally against the bias of respective bias members 38 and 62. Needle flange 50 will also move past trigger leg 94. Movement of flange 50 proximally past trigger leg 94 does not cause movement of latch 82 since there is no contact of trigger leg 92 with arm extension 86; and, accordingly, flange 50 is then positioned proximally of trigger leg 94 as shown in FIG. 2.

Upon entry into the anatomical cavity, the counterforce on the cannula and needle distal ends caused by tissue contact will be reduced allowing bias members 38 and 62 to move the cannula and needle distally. Distal movement of the needle causes flange 50 to engage trigger leg 94 and to pivot the trigger counterclockwise looking at FIG. 2 causing leg 92 to engage arm extension 86. The engagement of leg 92 with arm extension 86 causes arm 80 to move toward base 74 moving the latch 82 out of engagement with the rail member rearward wall 58 thereby allowing the retracting member 64 to cause the needle to move proximally to the retracted position wherein the needle distal end 48 is proximally spaced from the cannula distal end 30 to protect the sharp tip 53 of the needle as shown in FIG. 3. The needle unit 24 including the needle 42 can then be withdrawn from the catheter unit 22 leaving the cannula 26 in place within the anatomical cavity wall to serve as a portal for passage of fluids and medical instruments therethrough.

Figure 4:
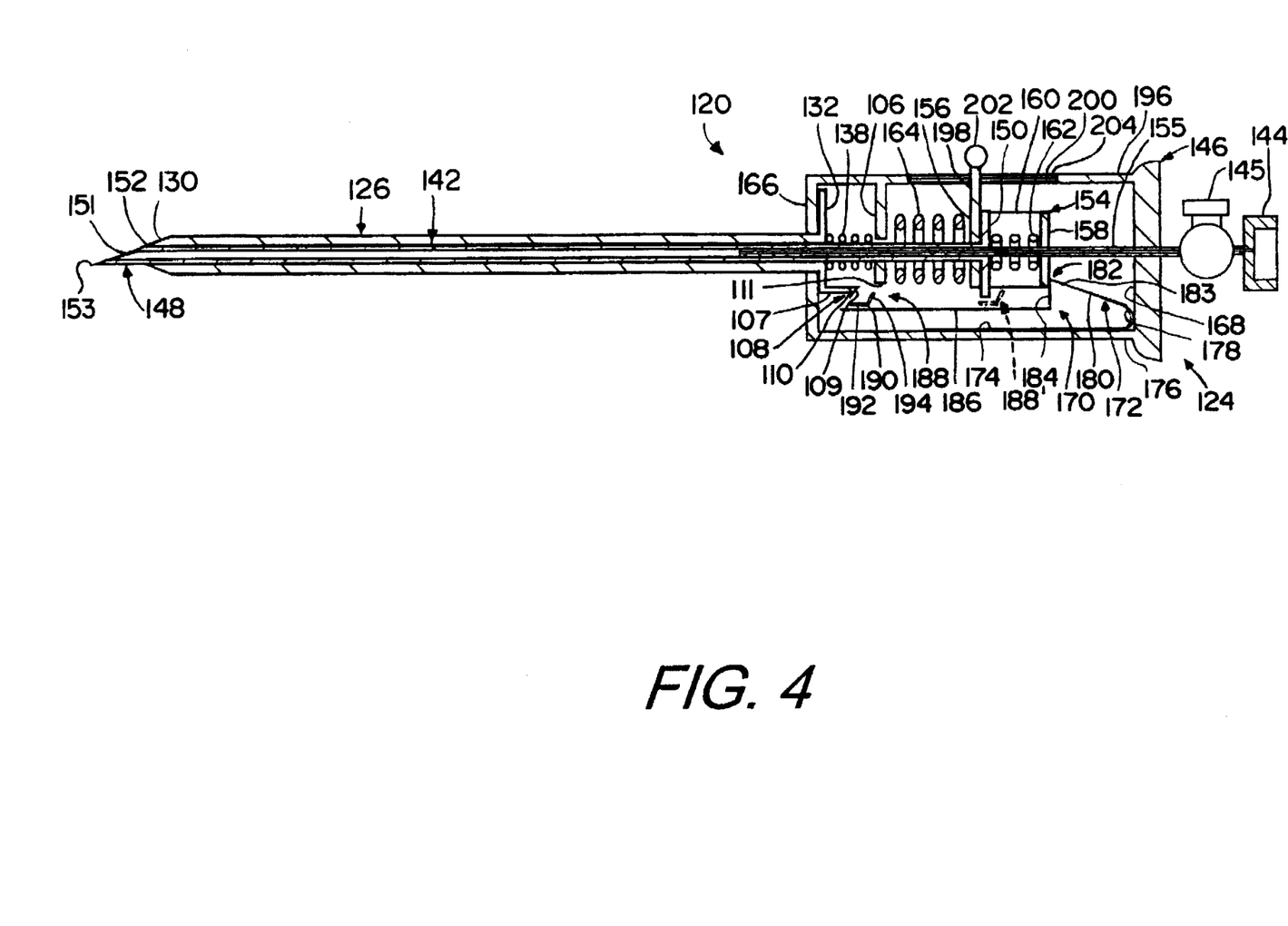
FIG. 4 is a side view, partly in section, of a modification of the safety needle instrument according to the present invention.

A modification of the safety needle instrument of the present invention is shown in FIG. 4 at 120. The modified safety needle instrument 120 is similar to safety needle instrument 20 except that movement of the needle to the retracted position is triggered by distally-biased movement of the cannula in response to a reduction in the force from tissue contact following entry into the anatomical cavity. Safety needle instrument 120 includes only a needle unit 124 having a cannula 126, a needle 142 and a hub 146 mounting proximal ends of the cannula and needle. Needle 142 is similar to needle 42 and terminates distally at a distal end 148 and proximally at a transverse flange 150 disposed between forward and rearward walls 156 and 158 of a rail member 154 disposed within the hub. The proximal end of the needle 142 is also telescopically fitted over a hollow guide tube 155 extending through the rear wall 168 of the hub 146 to a valve 145 and coupling 144 proximally spaced from the hub rear wall. The bias member 162 is similar to bias member 62 and is disposed around the guide tube 168 and held in compression between the needle flange 150 and the rearward wall of rail member 154. Cannula 126 is similar to cannula 26; however, flange 132 at the proximal end of the cannula is disposed between the hub front wall 166 and an inner wall or partition 106 proximally spaced from the hub front wall and perpendicular to a longitudinal axis of the safety needle instrument. A finger 107 extends proximally from the cannula flange 132 in the direction of partition 106 and carries an outwardly oriented barb or pawl 108 at a proximal end having an angled proximal surface 109 and a transverse or vertical distal surface 110 substantially parallel to flange 132. A bias member 138, like bias member 38 for safety needle instrument 20, is disposed around needle 142 and is held in compression between the cannula flange 132 and the hub partition 106. A retracting member 164, similar to retracting member 64, is also disposed around the needle 142 but is held in compression between the rail member forward wall 156 and the hub inner wall or partition 106.

An opening or gap 111 is formed in the hub partition 106 on the side of the hub mounting the locking and releasing mechanism 170 and is of an appropriate size and shape to permit passage of the finger 107 when the cannula 126 is moved. Locking and releasing mechanism 170 for the safety needle instrument 120 is similar to locking and releasing mechanism 70 for safety needle instrument 20 except that arm extension 186 for safety needle instrument 120 extends distally from a distal latching surface 184 through the opening 111 to be disposed alongside the finger 107 carried by the cannula flange 132. A trigger 188, similar to trigger 88 for safety needle instrument 20, is distally spaced from hub partition 106 and is pivotally mounted on a pin 190 secured to a wall or walls of the hub between arm extension 186 and the cannula flange 132. Trigger 188 is generally L-shaped with a leg 192 overlying extension 186 and a leg 194 extending transversely from leg 192 and toward the proximal end of the hub to be disposed proximally of the barb 108 at the proximal end of finger 107 when the cannula is in the extended rest position shown.

Operation of the safety needle instrument 120 is similar to that of safety needle instrument 20 with the exception that proximal movement of the cannula 126 in response to the force from tissue contact causes barb 108 to engage trigger leg 194 rotating the trigger 188 clockwise looking at FIG. 4. Trigger leg 192 is thus moved away from arm extension 186 such that latch 182 maintains the rail member 154 in the extended position and barb 108 is then positioned proximally of trigger leg 194. Upon penetrating into an anatomical cavity, distally-biased movement of the cannula 126 in response to a reduction in force caused by tissue contact causes the transverse distal surface 110 of the barb 108 to move distally into engagement with the trigger leg 94 causing the trigger 188 to rotate counterclockwise looking at FIG. 4 triggering release of the latch 182 from the rail member rearward wall 158 so that the needle 142 is moved proximally to the retracted position when the cannula enters the anatomical cavity.

Another modification of the safety needle instrument of the present invention is arrived at by mounting a second trigger in the needle unit 124, as shown in phantom at 188' in FIG. 4. The second trigger 188' is mounted within the hub 146 at a location similar to that of trigger 88 in needle unit 24 for being engaged by the needle flange 150. By providing a second trigger proximate the needle flange 150, movement of the needle to the retracted position can be achieved in response to distally-biased movement of either or both of the cannula and the needle upon entering an anatomical cavity. Operation of the modified needle unit is similar to that described above in connection with needle unit 124 with the exception that cannula and needle flanges are moved to positions proximally spaced from triggers 188 and 188' during penetration of an anatomical cavity wall and will move distally in response to a reduction in force from tissue contact upon entering the anatomical cavity. Distally-biased movement of either or both of the cannula 126 and the needle 142 causes one or both triggers to be rotated counterclockwise looking at FIG. 4 such that arm extension 186 of the locking spring 172 will be moved away from the longitudinal axis of the needle unit toward the base 174 of the locking spring to release latch 182 from the rail member 154. Retraction of the penetrating member can thus be assured even if one of the penetrating components is prevented from moving distally upon entering the anatomical cavity.

Figure 5:
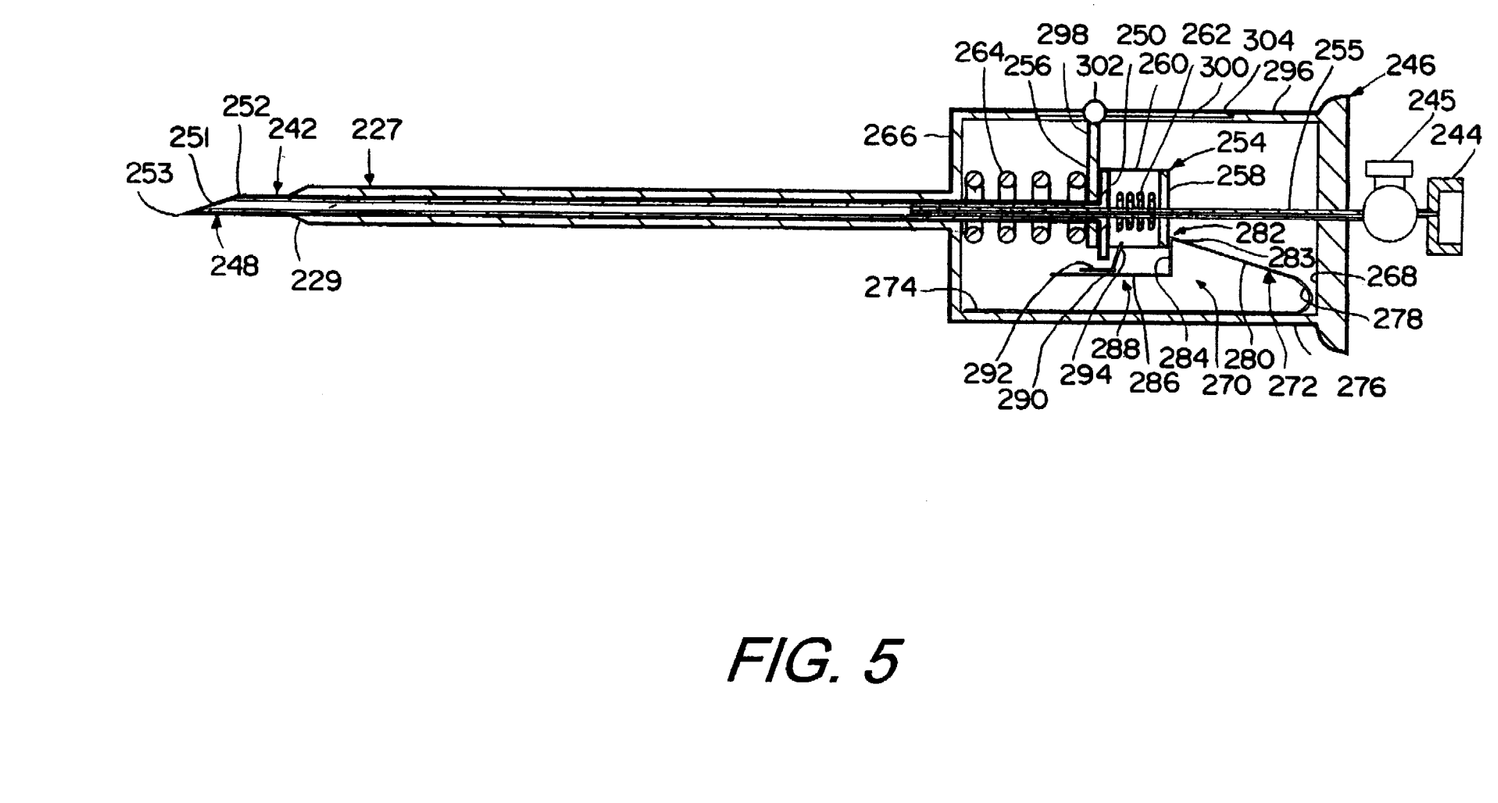
FIG. 5 is a side view, partly in section, of a modified penetrating unit for use with a safety needle instrument according to the present invention.

A modified needle unit for the safety needle instrument of the present invention is shown in FIG. 5 at 224. The modified needle unit 224 is similar to needle unit 24 for safety needle instrument 20 but with a protective sheath or sleeve 227 fixed to the front wall 266 of the hub 246. The protective sheath 227 extends distally from the front wall of the hub to terminate distally at a distal end 229. Needle 242 is disposed within the protective sheath 227 and, when the needle is in the locked extending position shown, the junction 252 of the needle is distally spaced from the distal end 229 of the protective sheath such that the needle junction can move into alignment with the distal end of the sheath in response to the force from tissue contact to ease penetration. With the needle in the retracted position, shown in phantom in FIG. 5, the distal end 248 of the needle is proximally spaced from the distal end 229 of the protective sheath so that the sharp distal tip 253 of the needle is protected by the sheath when the needle unit 224 is removed from a catheter unit such as catheter unit 22.

In the embodiments shown, the distal end of the cannula is aligned with a transverse dimensional transition or junction of the needle when the cannula is in a rest position and the needle is locked in the extended position prior to being used for penetrating an anatomical cavity wall; and since the needle and cannula are movable during penetration, the distal ends of the needle and cannula become displaced proximally relative to the housing and hub, with distally-biased movement of at least one of the needle and cannula triggering release of a latching mechanism to allow a retracting member to move the needle proximally to a retracted position where the tip of the needle is protected.

Figure 6:
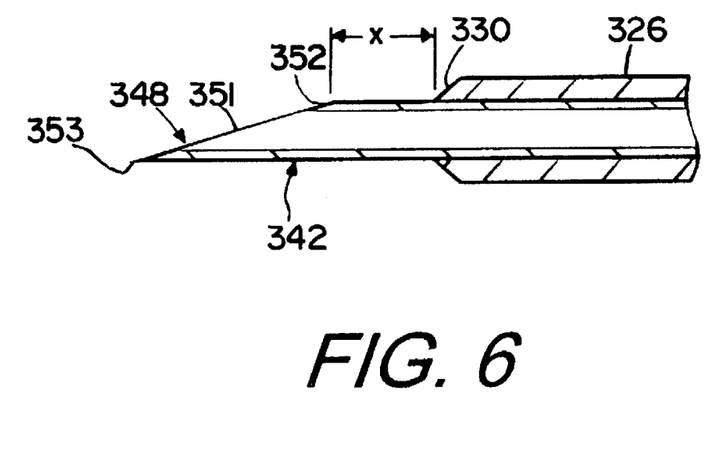
FIG. 6 is a fragmentary side view, partly in section, of an alternative distal end alignment for a safety needle instrument according to the present invention.

FIG. 6 shows an alternative distal configuration for the safety needle instruments of the present invention wherein the distal end 330 of the cannula is proximally spaced from the distal end junction 352 of the needle 342 a predetermined distance x when the cannula is in the rest position and the needle is locked in the extended position. In this configuration, the needle can move proximally during penetration towards becoming aligned with the cannula distal end to ease penetration by providing a smooth profile and can either stop or move together with the cannula as penetration continues. Upon entering into an anatomical cavity, both the needle and the cannula will spring back toward their original positions with the distally-biased movement of one or both of the cannula and needle triggering release of the latch holding the needle to permit the retracting member to move the needle proximally to the retracted position where the sharp tip 353 of the needle is protected.

Figure 7:
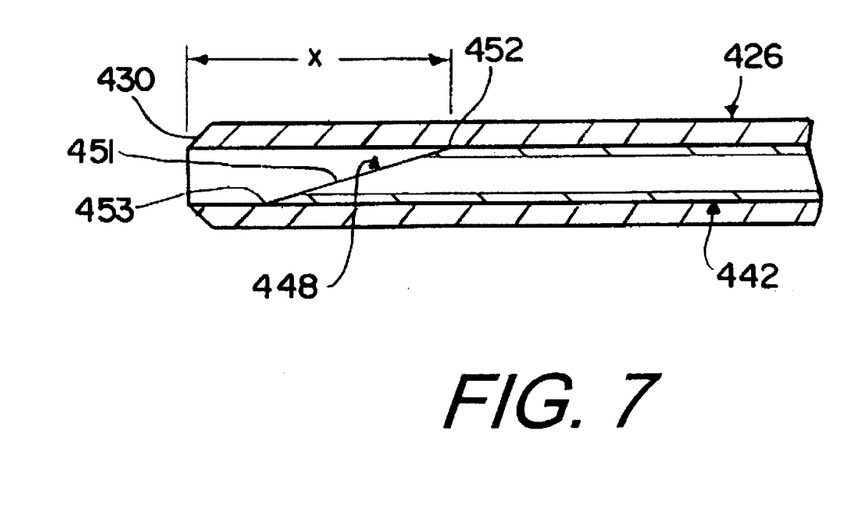
FIG. 7 is a fragmentary side view, partly in section, of another alternative distal end alignment for a safety needle instrument according to the present invention.

Another distal configuration for the safety needle instruments of the present invention is shown in FIG. 7 wherein the distal end 430 of the cannula is distally spaced from the distal end junction 452 of the needle 442 a predetermined distance x when the cannula is in the rest position and the needle is locked in the extended position. In this configuration, the cannula can move proximally during penetration towards becoming aligned with the needle distal end junction to ease penetration by providing a smooth profile and can move together with the needle as penetration continues. Upon entering into an anatomical cavity, both the needle and the cannula will spring back toward their original positions with the distally-biased movement of one or both of the cannula and needle triggering release of the latch holding the needle to permit the retracting member to move the needle proximally to the retracted position where the sharp tip 453 of the needle is protected.

From the above, it will be appreciated that the cannula and needle of the safety needle instrument of the present invention are movable proximally during penetration of an anatomical cavity wall and distally upon entering the anatomical cavity to trigger retraction of the needle to a position where the distal end of the needle is protected. Retraction of the needle can be conditioned upon distally-biased movement of the cannula, the needle or both the cannula and the needle. Furthermore, distal ends of the cannula and the needle can be aligned prior to penetration to define a smooth distal profile for penetrating anatomical tissue, which profile can be substantially maintained during penetration by permitting proximal movement of the needle and the cannula. Alternatively, the distal end of the cannula can be distally or proximally spaced from the needle distal end such that movement of the cannula and/or needle in response to tissue contact will cause the distal ends of the cannula and needle to become substantially aligned. If the cannula distal end is distally spaced from the needle distal end in the extended rest position, the cannula can also function as a safety member to protect the needle distal end in the event that the needle is not retracted.

The components of the safety needle instrument of the present invention can be made of any suitable, medical grade materials to permit sterilization for re-use or for single patient use. The components can be made of multiple parts of various configurations and materials to reduce cost. The catheter unit and/or needle unit can have various valves, stop cocks and seals disposed therein to control fluid flow therethrough, and conventional detent mechanisms can be used to connect or latch the hub with the housing when the catheter unit and the needle unit are assembled. The distal end of the cannula can be chamfered or blunt, smooth or roughened, or have any other configuration depending on the need for ease of penetration or increased resistance. Also, the strength of the bias members biasing the cannula and needle can be chosen according to differences in the resistant forces acting on the cannula and needle in order to maintain a substantially smooth distal profile during penetration.

Figure 8:
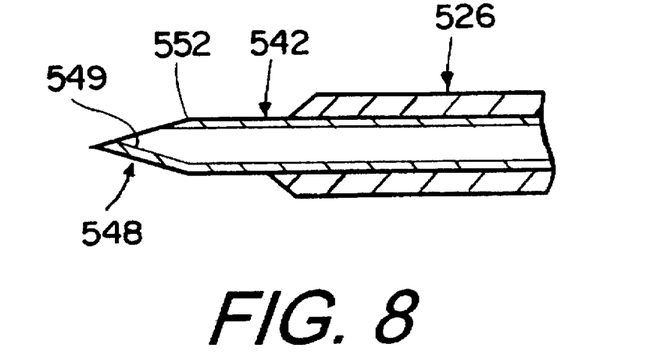
FIGS. 8 and 9 are fragmentary side views of modified distal ends for the needle of a safety needle instrument according to the present invention.
Figure 9:
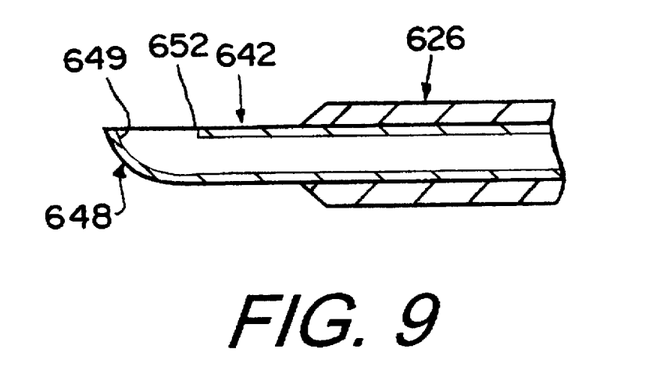

The distal end of the needle can have any desired configuration suitable for defining a distal opening and for penetrating anatomical tissue, such as, for example, the beveled or slanted configuration previously described, a conical or pyramidal distal configuration 548 with an aperture or opening 549 on the tapered portion of the distal end as shown in FIG. 8, or a curved distal end 648 with a transverse or side-facing opening 649 as shown in FIG. 9. Additionally, the surface defining the distal end of the needle can be irregular or smooth, continuous or disjointed, provided with cutting features or having any combination of the above.

Figure 10:
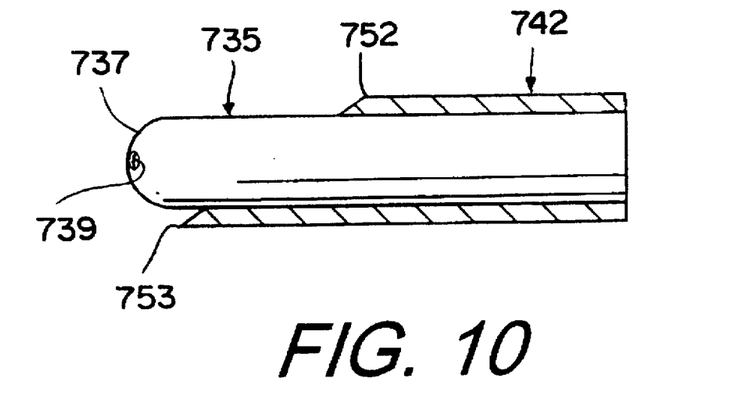
FIG. 10 is a fragmentary side view, partly in section, of a safety probe for use with the safety needle instrument of the present invention.

FIG. 10 shows a modification of the safety needle instrument of the present invention wherein the modified safety needle instrument 720 includes a hollow needle 742 and a cylindrical safety probe 735 disposed within the needle and movable between an extended protruding position protecting the distal end 748 of the needle and a retracted position exposing the sharp tip 753 of the needle. The safety probe 735 is distally-biased and has a rounded distal end 737 with an opening 739 formed therein for permitting passage of fluids through the needle. It will be appreciated that the safety probe can be mounted in the hub or housing of any of the safety needle instruments shown and that a flange or other type of protrusion can be carried at the safety probe proximal end and either passed through a slot or opening in the penetrating member or disposed proximally of the rail member to serve as an operating member for triggering retraction of the needle in response to distally-biased movement of the probe in response to a reduction in force caused by tissue contact upon entering an anatomical cavity. The safety probe distal end can have any configuration to protrude through single or multiple openings formed in the distal end of the needle and can conform to the distal profile of the needle when retracted or present a discontinuous surface when retracted.

The rail member can have various configurations to engage the latch and be released by the trigger. Preferably, the rail member will have a configuration to serve as a stop or abutment for the needle as exemplified herein by a U-shaped rail member.

The locking and releasing mechanisms require only a latch for locking the needle in the extended position and a trigger for releasing the latch in response to distal movement of an operating member such as a flange carried by the needle and/or cannula; and, thus, it will be appreciated that various mechanisms can be employed to produce the locking and releasing functions such as, for example, multiple movably or pivotally mounted cams or pawls. It will be appreciated that the locking and releasing mechanism can be designed and arranged in the housing or the hub in various ways to minimize the length of the housing or the hub and, therefore, the overall length of the housing and hub. Various locking and releasing mechanisms that can be simply modified for use in the safety needle instrument of the present invention are disclosed in U.S. Pat. Nos. 5,330,432; 5,324, 268; 5,320,610; 5,336,176; and 5,360,405 to Yoon and Applicant's pending applications Ser. No. 07/848,838, filed Mar. 10, 1992; Ser. No. 07/845,177, filed Sep. 15, 1992; Ser. No. 07/945,177, filed Sep. 15, 1992; Ser. No. 08/079,586, filed Jun. 22, 1993; Ser. No. 08/195,512, filed Feb. 14, 1994; Ser. No. 08/196,029, filed Feb. 14, 1994; Ser. No. 08/196, 027, filed Feb. 14, 1994; Ser. No. 08/195,178, filed Feb. 14, 1994; Ser. No. 08/237,734, filed May 4, 1994; Ser. No. 08/247,205, filed May 20, 1994; Ser. No. 08/254,007, filed Jun. 3, 1994; and Ser. No. 08/260,439, filed Jun. 15, 1994. The disclosures of the above-listed issued patents and pending patent applications are incorporated herein by reference. The issued patents and applications listed above also disclose various bias arrangements useful with the safety needle instrument of the present invention. Other locking and releasing mechanisms that can be used in the safety needle instrument of the present invention are disclosed in Applicant's pending applications Ser. Nos. 08/279,170 and 08/279,172, filed Jul. 22, 1994, the disclosures of which are incorporated herein by reference.

One or more control buttons, such as the control buttons described in Applicant's copending patent application, Ser. No. 08/083,220, filed Jun. 24, 1993, can be mounted next to any latch for manually disengaging the latch to prevent locking of the needle in the extended position. Furthermore, additional latches can be provided or existing latches modified to carry pawls or form latching surfaces for locking a needle in the retracted position and can then be released through the use of a control button as described above to permit the needle to be moved distally to the locked extended position prior to use.

It will also be appreciated that after penetration of the safety needle instrument into the anatomical cavity, the distally-biased cannula can act as a shock absorber upon inadvertent contact with tissue. The distal bias for the triggering member (i.e., the cannula, needle, and/or probe) of the safety needle instrument need only be strong enough to allow slight movement of the member during penetration such that the force-to-penetrate can be minimized.

The features of the various embodiments described above can be combined in any manner desired dependent upon the requirements and complexity of the safety needle instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety needle instrument for establishing a portal in the wall of an anatomical cavity comprising a housing;

an elongate cannula having a proximal end mounted by said housing and a distal end for introduction in the anatomical cavity, said cannula being movable relative to said housing during penetration between an extended rest position and a retracted position;

cannula bias means for biasing said cannula distally relative to said housing toward said rest position;

a needle disposed within said cannula and having a distal end for penetrating the anatomical cavity wall, said needle being movable relative to said housing between an extended position and a retracted position where said needle distal end is proximally spaced from said cannula distal end;

retracting means for moving said needle from said needle extended position to said needle retracted position;

means for manually moving said needle from said needle retracted position to said needle extended position;

locking means for locking said needle in said needle extended position while permitting a predetermined amount of proximal movement of said needle relative to said housing during penetration of the anatomical cavity wall;

needle bias means for biasing said needle distally relative to said housing in said needle extended position while permitting proximal movement of said needle during penetration of the anatomical cavity wall; and releasing means responsive to penetration of said safety needle instrument into the anatomical cavity for triggering release of said locking means to permit said retracting means to move said needle proximally to said needle retracted position.

2. A safety needle instrument as recited in claim 1 wherein said releasing means is responsive to distally-biased movement of said cannula upon penetrating into the anatomical cavity.

3. A safety needle instrument as recited in claim 2 and further comprising a rail member mounting a proximal end of said needle, wherein said proximal end of said needle includes a flange movable within said rail member, said proximal end of said cannula carries an operating member, said locking means includes a latch spring engaging said rail member to lock said needle in said extended position and said releasing means includes a trigger responsive to distally-biased movement of said operating member for releasing said latch spring.

4. A safety needle instrument as recited in claim 1 wherein said releasing means is responsive to distally-biased movement of said needle upon penetrating into the anatomical cavity.

5. A safety needle instrument as recited in claim 1 wherein said releasing means is responsive to distally-biased movement of said cannula and said needle upon penetrating into the anatomical cavity.

6. A safety needle instrument as recited in claim 5 and further comprising a hub and a rail member movably disposed within said hub for mounting a proximal end of said needle, wherein said proximal end of said needle includes a flange movable within said rail member, said proximal end of said cannula carries an operating member, said locking means includes a latch spring disposed within said hub for engaging said rail member to lock said needle in said extended position and said releasing means includes a trigger responsive to distally-biased movement of said needle flange and said operating member for releasing said latch spring.

7. A safety needle instrument as recited in claim 1 wherein said needle distal end extends distally from a junction where a transverse dimension of said needle changes and wherein said cannula distal end is aligned with said junction when said needle and said cannula are in said respective extended positions.

8. A safety needle instrument as recited in claim 1 wherein said needle distal end extends distally from a junction where a transverse dimension of said needle changes and wherein said cannula distal end is located proximally of said junction when said needle and said cannula are in said respective extended positions.

9. A safety needle instrument as recited in claim 1 wherein said needle distal end extends distally from a junction where a transverse dimension of said needle changes and wherein said cannula distal end is located distally of said junction when said needle and said cannula are in said respective extended positions.

10. A safety needle instrument as recited in claim 1 and further comprising a hub mounting a proximal end of said needle, said hub being configured to detachably mate with said housing.

11. A safety needle instrument as recited in claim 10 and further comprising a protective sheath fixed to said hub and disposed between said cannula and said needle when said hub is mated with said housing, said protective sheath having a distal end proximally spaced from said needle distal end when said needle is extended and distally spaced from said needle distal end when said needle is retracted.

12. A safety needle instrument for establishing a portal in the wall of an anatomical cavity comprising a housing;

an elongate cannula having a proximal end mounted by said housing and a distal end for introduction in the anatomical cavity, said cannula being movable relative to said housing between an extended rest position and a retracted position;

cannula bias means for biasing said cannula distally toward said rest position;

a needle disposed within said cannula and having a distal end for penetrating the anatomical cavity wall, said needle being movable relative to said cannula between an extended position and a retracted position where said needle distal end is proximally spaced from said cannula distal end;

retracting means for moving said needle from said needle extended position to said needle retracted position;

means for manually moving said needle from said needle retracted position to said needle extended position;

locking means for locking said needle in said needle extended position while permitting a predetermined amount of proximal movement of said needle during penetration of the anatomical cavity wall;

needle bias means for biasing said needle distally in said needle extended position while permitting proximal movement of said needle during penetration of the anatomical cavity wall;

releasing means responsive to penetration of said safety needle instrument into the anatomical cavity for triggering release of said locking means to permit said retracting means to move said needle proximally to said needle retracted position, wherein said releasing means is responsive to distally-biased movement of said needle upon penetrating into the anatomical cavity; and a rail member mounting a proximal end of said needle, wherein said proximal end of said needle includes a flange movable within said rail member, said locking means includes a latch spring engaging said rail member to lock said needle in said extended position and said releasing means includes a trigger responsive to distally-biased movement of said needle flange for releasing said latch spring.

* * * * *